(12) United States Patent
Smart et al.

(10) Patent No.: US 9,574,236 B2
(45) Date of Patent: Feb. 21, 2017

(54) ISOLATION OF RNA-PROTEIN COMPLEXES USING CROSS-LINKING REAGENTS AND OLIGONUCLEOTIDES

(71) Applicant: Agilent Technologies, Inc., Loveland, CO (US)

(72) Inventors: Brian Phillip Smart, San Jose, CA (US); Robert A. Ach, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 215 days.

(21) Appl. No.: 14/590,869

(22) Filed: Jan. 6, 2015

(65) Prior Publication Data

US 2015/0125862 A1    May 7, 2015

Related U.S. Application Data

(62) Division of application No. 13/267,702, filed on Oct. 6, 2011, now Pat. No. 8,951,804.

(60) Provisional application No. 61/410,247, filed on Nov. 4, 2010.

(51) Int. Cl.
   *G01N 33/68*     (2006.01)
   *C12Q 1/68*      (2006.01)
   *G01N 33/53*     (2006.01)

(52) U.S. Cl.
   CPC .......... *C12Q 1/6876* (2013.01); *C12Q 1/6844* (2013.01); *G01N 33/5308* (2013.01); *G01N 33/6803* (2013.01); *G01N 33/6848* (2013.01); *C12Q 2600/158* (2013.01); *C12Q 2600/178* (2013.01); *Y10T 436/143333* (2015.01)

(58) Field of Classification Search
   USPC .......................................................... 436/86
   See application file for complete search history.

(56) References Cited

U.S. PATENT DOCUMENTS

| | | |
|---|---|---|
| 8,642,744 B2 | 2/2014 | Smart et al. |
| 2004/0038331 A1 | 2/2004 | Reddy et al. |
| 2006/0094121 A1 | 5/2006 | Reid et al. |
| 2006/0115871 A1 | 6/2006 | Bruce et al. |
| 2009/0053817 A1 | 2/2009 | Reid et al. |
| 2010/0105145 A1 | 4/2010 | Winther |

OTHER PUBLICATIONS

Amunugama, et al., "Mechanisms for the Selective Gas-Phase Fragmentation Reactions of Methionine Side Chain Fixed Charge Sulfonium Ion Containing Peptides", Journal of the American Society for Mass Spectrometry, 2006, 17:1631-42.

(Continued)

*Primary Examiner* — Yelena G Gakh
*Assistant Examiner* — Michelle Adams

(57) ABSTRACT

Provided herein is a method of sample analysis. In certain embodiments, the method comprises: a) cross-linking protein of a cell using a first compound to produce a first cross-linked product comprising cross-linked protein and RNA; b) contacting the first cross-linked product and a second compound under conditions by which an oligonucleotide portion of the second compound hybridizes to the RNA; c) activating a reaction the first and second compound, thereby covalently crosslinking the oligonucleotide to the cross-linked protein to produce a second cross-linked product; d) isolating the second cross-linked product using an affinity tag; and e) analyzing the isolated second cross-linked product. Compounds for performing the method are also provided.

10 Claims, 1 Drawing Sheet

(56) References Cited

OTHER PUBLICATIONS

Hogg, et al., "RNA-based affinity purification reveals 7SK RNPs with distinct composition and regulation", RNA, 2007, 13:868-80.
Leitner, et al., "Probing Native Protein Structures by Chemical Cross-linking, Mass Spectrometry, and Bioinformatics", Mol. Cell Proteomics, 2010, 9:1634-49.
Puig, et al., "The tandem affinity purification (TAP) method: a general procedure of protein complex purification", Methods, 2001, 24:218-29.
Rinner, et al., "Identification of Cross-linked Peptides from Large Sequence Databases", Nat. Methods, 2008, 5:315-8.
Zhang, et al., "Identification of Protein-Protein Interactions and Topologies in Living Cells with Chemical Cross-linking and Mass Spectrometry", Mol. Cell Proteomics, 2009, 8:409-20.
Zielinski, et al., "In vivo identification of ribonucleoprotein-RNA interactions", Proceedings of the National Academy of Sciences of the United States of America, 2006, 103:1557-62.

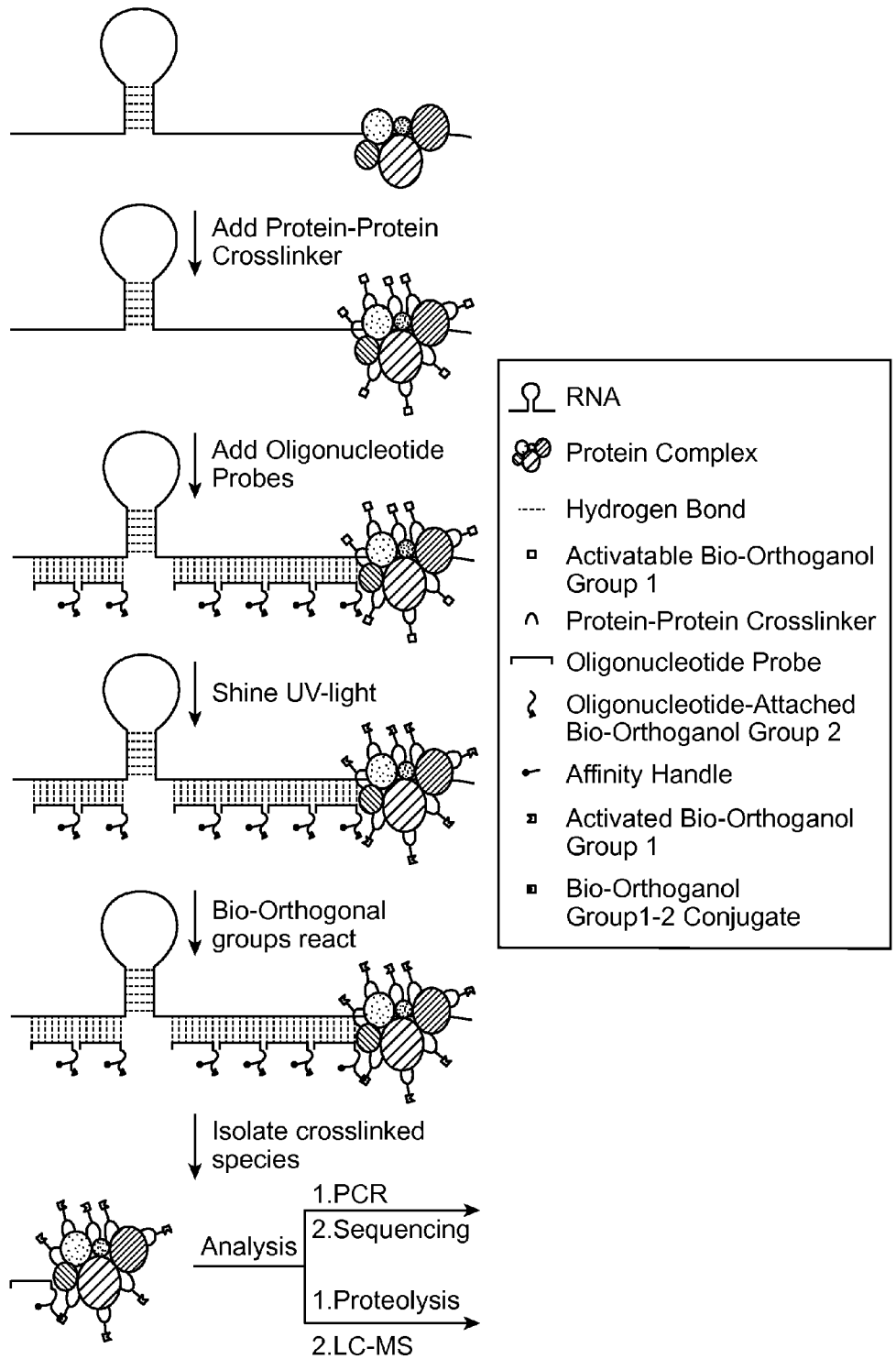

ISOLATION OF RNA-PROTEIN COMPLEXES USING CROSS-LINKING REAGENTS AND OLIGONUCLEOTIDES

CROSS REFERENCE TO RELATED APPLICATIONS

This application is a divisional of U.S. patent application Ser. No. 13/267,702, filed Oct. 6, 2011, which claims the benefit of U.S. Provisional Patent Application Ser. No. 61/410,247, filed on Nov. 4, 2010, all of which are incorporated by reference herein in their entirety.

INTRODUCTION

In recent years interest in the multitude of roles RNA plays in the cell has grown rapidly with the discovery of large numbers of non-coding RNAs (ncRNAs) of various lengths and subcellular locations. While RNA can function as both a structural and catalytic molecule, many of the roles these ncRNAs play in the cell will almost certainly involve proteins, as most cellular RNAs are bound to proteins in ribonucleoprotein particles. Thus, it is of great interest to researchers to isolate and characterize the proteins that are bound to a particular RNA.

SUMMARY

Provided herein is a method of sample analysis. In certain embodiments, the method comprises: a) cross-linking protein of a cell using a first compound to produce a first cross-linked product comprising cross-linked protein, and RNA; b) contacting the first cross-linked product and a second compound under conditions by which an oligonucleotide portion of the second compound hybridizes to the RNA; c) activating a reaction between the first and second compound, thereby covalently crosslinking the oligonucleotide to the cross-linked protein to produce a second cross-linked product; d) isolating the second cross-linked product using an affinity tag; and e) analyzing the isolated second cross-linked product. Compounds for performing the method are also provided.

BRIEF DESCRIPTION OF THE FIGURES

FIG. 1 illustrates the general principle of certain embodiments of the subject method.

DEFINITIONS

Unless defined otherwise, all technical and scientific terms used herein have the same meaning as commonly understood by one of ordinary skill in the art to which this invention belongs. Still, certain terms are defined below for the sake of clarity and ease of reference.

As used herein, the term "affinity tag" refers to a member of a specific binding pair, i.e. two molecules where one of the molecules through chemical or physical means specifically binds to the other molecule. The complementary member of the specific binding pair may be immobilized (e.g., to a chromatography support, a bead or a planar surface) to produce an affinity chromatography support that specifically binds the affinity agent. Tagging a compound of interest with an affinity agent allows the compound to be separated from a mixture of untagged compounds using affinity chromatography. The specific binding pair are sometimes referred to as a ligand and receptor, although two complementary polynucleotide sequences (including nucleic acid sequences used as probes and capture agents in DNA hybridization assays) are also specific binding pairs, as are antibody and antigen, peptide-MHC antigen and T cell receptor, biotin and streptavidin pairs, etc. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc., so long as an epitope is present.

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEG$_n$-Biotin where n is 3-12.

As used herein, the term "cleavable" in the context of "cleavable bond" refers to a covalent bond in a molecule that can be selectively cleaved to produce two products. Application of a suitable cleavage stimulus to a molecule that contains more than one cleavable bonds that are cleaved by the stimulus will produce more than two products.

As used herein, the term "cleavage conditions" refers to the conditions in which a cleavable bond may be selectively cleaved. Ionization conditions that do not fragment peptide backbones are an example of a cleavage condition.

As used herein, the term "heterosubstituted carbonyl group" refers to a carbonyl group —C(=O)— in which the carbonyl oxygen is replaced by another heteroatom having at least one lone pair of electrons. Examples of heterosubstituted carbonyl groups include the group —C(=Y)—, where Y is S or NR$^3$ and R$^3$ is selected from hydrogen and an alkyl. Such a group may participate in a reaction that occurs via a nucleophilic substitution reaction of the heteroatoms containing at least one lone pair of electrons with atoms that are adjacent to the sulphonium or phosphonium leaving groups to break the covalent bonds adjacent to the sulphonium or phosphonium leaving groups, releasing two peptide-containing products that are each positively charged.

As used herein, the term "ionization conditions that do not fragment peptide backbones" and grammatical equivalents thereof refer to ionization conditions having an energy that is insufficient to significantly cleave any of the bonds in the peptide backbone of [Glu1]-fibrinopeptide B. One example of such conditions are the conditions inside the ion source of an Agilent 6520 series QTOF mass spectrometer, operating under standard parameters for peptide analysis, in which a so-called "in-source" potential of 250 Volts is applied. The energy required to provide such conditions may vary greatly depending on the manufacturer and design of the mass spectrometer system used. Such conditions may also may be produced in other parts of a mass spectrometry system, e.g., in a collision cell.

Certain embodiments described in this disclosure may refer to a bond that is cleavable in ionization conditions that do not fragment peptide backbones. In these embodiments, the bond is cleaved at an energy that is insufficient to significantly cleave any of the bonds in the peptide backbone of [Glu1]-fibrinopeptide B. An example of such conditions is described above. An example of such a cleavable bond is the bond that is present between a sulphonium group and the adjacent carbon of a linker in a crosslinked compound, e.g., a —CH$_2$—S$^+$(CH$_3$)— cleavable bond.

As used herein, the term "linking moiety" refers to a moiety that links other functional groups together. One example of a linking moiety is a trifunctional scaffold, which is a moiety that contains three linkages to three distinct linked groups. A trifunctional scaffold may be a single atom or a group containing 30 carbons or less. Examplary trifunctional scaffolds include: 1) an aryl group (e.g., a phenyl group) that includes three substituents that each connect to one of the linked groups; 2) a trisubstituted nitrogen atom; and 3) an amino acid where the amino group, the carboxylic acid group and the sidechain group of the amino acid each connect to one of the linked groups.

As used herein, the term "linker" or "linkage" refers to a linking moiety that connects two groups and has a backbone of 20 atoms or less in length. A linker or linkage may be a covalent bond that connects two groups or a chain of between 1 and 20 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated. Usually no more than one, two, or three unsaturated bonds will be present in a linker backbone. The linker may include one or more substituent groups, for example an alkyl, aryl or alkenyl group. A linker may include, without limitations, oligo(ethylene glycol), ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the term "cleavable linker" refers to a linker that can be selectively cleaved to produce two products. Application of suitable cleavage conditions to a molecule containing a cleavable linker that is cleaved by the cleavage conditions will produce two cleavage products. A cleavable linker of the present invention is stable, e.g. to physiological conditions, until it is contacted with a reagent capable of cleaving the cleavable linker.

For clarity, the number of atoms that connect two groups is calculated by counting the minimum number of covalently linked atoms between the two groups, excluding atoms of the two groups themselves. When the linkage between two groups includes a cyclic moiety, the shortest path around the ring of the cyclic moiety is counted so that a minimum possible number of atoms that connect the two groups is calculated.

As used herein, the term "substituted" refers to a group in which one or more atoms of the group are each independently replaced with a substituent(s), where the atom being replaced may be a hydrogen or non-hydrogen atom (e.g., a carbon or a heteroatom). A group that is "substituted" can have 1 or more substituents, where the substituents are independently selected from the group consisting of acyl, acylamino, acyloxy, alkoxy, alkoxycarbonyl, alkoxycarbonylamino, alkyl, trihaloalkyl, alkenyl, alkynyl, amino, amido, imino, aminocarbonyl, aminocarbonylamino, aminocarbonyloxy, aryl, aryloxy, azido, carboxyl, carbonyl, cyano, isocyanate, isothiocyanate, cycloalkyl, guanidyl, halogen, heterocyclyl, heterocyclyloxy, hydroxyl, keto, nitro, nitroso, oxo, thio, thioether, thioalkoxy, thioaryloxy, thioketo, thiol, sulfonate, sulfinate, phosphinate, phosphonate, alkyl-S(O)—, aryl-S(O)—, alkyl-S(O)$_2$— and aryl-S(O)$_2$.

As used herein, the term "protein linking group" refers to a group that is capable of reacting directly either spontaneously or after activation through contact with a stimulus, e.g., light, with an accessible sidechain functional group of a protein under aqueous conditions to produce a covalent linkage to the protein. The protein linking group is capable of reacting under aqueous conditions at which proteins of interest are able to be maintained in a folded state (e.g., physiological conditions). The protein linking group is capable of reaction with one or more functional groups of a protein of interest, such as a sidechain group of a Lys, Cys, Ser, Thr, Tyr, His or Arg amino acid residue of the protein, i.e., the protein linking group may be amino-reactive, thiol-reactive, hydroxyl-reactive, imidazolyl-reactive or guanidinyl-reactive. Exemplary protein linking groups include active esters (e.g., an amino-reactive NHS ester), and thiol-reactive maleimide or iodoacetamide groups. Further exemplary protein linking groups and methods of using the same are described in Hermanson, "Bioconjugate Techniques" 2nd Edition, Academic Press, 2008.

As used herein, the term "crosslinking" refers to a reaction in which a covalent bond is formed.

As used herein, the term "covalently crosslinked" refers to two moieties that are linked to each other via covalent bonds.

As used herein, the term "leaving group" refers to a group that is capable of being disconnected from an adjacent atom during a nucleophilic substitution reaction or a nucleophilic acyl substitution reaction at that adjacent atom. Exemplary leaving groups include the N-hydroxysuccinimidyl group of an NHS ester, and the sulfonium group of the cleavable bond described above.

The compounds of the invention may contain one or more asymmetric centers and may thus give rise to enantiomers, diastereomers, and other stereoisomeric forms that may be defined in terms of absolute stereochemistry as (R)- or (S)- or, as (D)- or (L)- for amino acids. The present invention is meant to include all such possible isomers as well as their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the terms "polypeptide" and "protein" are used interchangeably. The term "polypeptide" also includes post translational modified polypeptides or proteins. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids. In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 9, 10, 20, 30 or 50 amino acids. In some embodiments, peptides are between 5 and 30 amino acids in length. A peptide may be made by protease digestion of a large polypeptide.

The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. Typically, "complementary" refers to a nucleotide sequence that is fully complementary to a target of interest such that every nucleotide in the sequence is complementary to every nucleotide in the target nucleic acid in the corresponding positions. When a nucleotide sequence is not fully complementary (100% complementary) to a non-target sequence but still may base pair to the non-target sequence due to complementarity of certain stretches of nucleotide sequence to the non-target sequence, percent complementarity may be calculated to assess the possibility of a non-specific (off-target) binding. In general, a complementarity of 50% or less does not lead to non-specific binding. In addition, a complementarity of 70% or less may not lead to non-specific binding under stringent hybridization conditions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from 2 to 200 nucleotides (e.g., 25 to 200 nucleotides) and up to 500 nucleotides in length. Oligonucleotides may be synthetic and, in certain embodiments, are less than 300 nucleotides in length. Oligonucleotides may be 10 to 20, 11 to 30, 31 to 40, 41 to 50, 51-60, 61 to 70, 71 to 80, 80 to 100, 100 to 150 or 150 to 200, up to 500 or more nucleotides in length, for example.

The term "sample" as used herein relates to a material or mixture of materials, typically, although not necessarily, in fluid form, containing one or more components of interest.

The term "hybridization" refers to the specific binding of a nucleic acid to a complementary nucleic acid via Watson-Crick base pairing. Accordingly, the term "in situ hybridization" refers to specific binding of a nucleic acid to a metaphase or interphase chromosome.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. Stringent assay conditions are the summation or combination (totality) of both hybridization and wash conditions.

A "stringent hybridization" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions determines whether a nucleic acid is specifically hybridized to a probe. Wash conditions used to identify nucleic acids may include, e.g.: a salt concentration of about 0.02 molar at pH 7 and a temperature of at least about 50° C. or about 55° C. to about 60° C., a salt concentration of about 0.15 M NaCl at 72° C. for about 15 minutes, or a salt concentration of about 0.2×SSC at a temperature of at least about 50° C. or about 55° C. to about 60° C. for about 15 to about 20 minutes. Alternatively, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA, or the like.

The terms "hybridizing" and "binding", with respect to nucleic acids, are used interchangeably.

The terms "plurality", "set" or "population" are used interchangeably to mean at least 2, at least 10, at least 100, at least 500, at least 1000, at least 10,000, at least 100,000, at least 1,000,000, at least 10,000,000, at least 100,000,000, or more.

The phrase "tiled probes" refers to overlapping and non-overlapping probes that are designed to span or "tile" across an RNA of interest. Non-overlapping tiled probes may be end-to-end tiled with no bases separating them or they may be spaced farther apart.

Before the present invention is described in greater detail, it is to be understood that this invention is not limited to particular embodiments described, and as such may vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

The headings provided herein are not limitations of the various aspects or embodiments of the invention. Accordingly, the terms defined immediately below are more fully defined by reference to the specification as a whole.

DETAILED DESCRIPTION OF EXEMPLARY EMBODIMENTS

The general principles of the subject method are illustrated in FIG. 1. In general terms, a protein-protein crosslinker is added to a sample containing an RNA/protein complex. The protein-protein crosslinker (which will be referred to as "compound I" in the detailed description that follows below) may be homo-bifunctional or hetero-bifunctional in that it reacts with the same or different amino acid side chains. Exemplary protein reactive groups include bis-NHS esters and maleimides, which react with amines and thiols, respectively. The use of such groups is known in the art. The protein-protein crosslinker also contains another reactive group that, upon activation, covalently links with a second reagent used later in the protocol. In particular embodiments, this reactive group may be a protected amino-oxy group or hydrazide group. Such a group can be deprotected by UV-light, e.g., if it is protected by nitrobenzyl carbamate, for example. In certain embodiments, this step is non-specific in that it does not target specific protein-protein complexes. Depending on the design of the protein-protein crosslinker, the crosslinker may crosslink accessible amino acids that are within 10 Å to 50 Å (e.g., 15 Å to 30 Å) of one another. The result of this step is referenced herein as a "first cross-linked product".

After the proteins have been crosslinked to each other to produce a first cross-linked product, an oligonucleotide probe (which will be referred to as "compound II" in the detailed description that follows below) that contains: a) a sequence of oligonucleotides that specifically hybridizes to an RNA; b) a group that is reactive with the reactive group of the protein-protein crosslinker (which may be an aldehyde if a protected amino-oxy group or hydrazide group is employed on the protein-protein crosslinker); and c) an affinity tag (e.g., biotin or the like) is contacted with the first cross-linked product under conditions suitable for the oligonucleotide in the oligonucleotide portion of the oligonucleotide probe to specifically hybridize to a RNA target. The RNA target may be any type of RNA, including but not limited to mRNA, rRNA, tRNA and small RNA (e.g., miRNA etc). In certain embodiments excess probe that has not been hybridized can be removed by size exclusion (e.g., using a membrane with a molecular weight cutoff) or at least diluted to a lower concentration.

Crosslinking of the oligonucleotide probe to the first cross-linked product can be accomplished by any of a number of different ways depending on the design of the protein-protein crosslinker and the oligonucleotide probe. For example, cross-linking may be triggered by any of a number of different methods including by addition of a catalyst, by deprotection of one or more of the reactive groups, or by some other means of activation (e.g., by altering the pH or the like). Examples of such chemistries are provided below. In the example shown, UV-light may be used to deprotect an amino-oxy or hydrazide groups in the protein-protein crosslinker. This step may be performed in a diluted environment if excess probe has not been removed by size exclusion to reduce the likelihood of unhybridized probes reacting with the protein-protein crosslinkers. Again, depending on which compounds are used, the reactive group of the oligonucleotide probe may react with reactive groups on the protein-protein crosslinker that are within 10 Å to 50 Å (e.g., 15 Å to 30 Å), thereby allowing only first cross-linked products that are proximal to the hybridized oligonucleotide to be linked to the hybridized oligonucleotide. The chemistry of the reaction between the reactive groups on the protein-protein crosslinker and the oligonucleotide probe is chosen so that it is specific in that the groups react with one another to form a covalent bond that is stable (i.e., irreversible under physiological conditions) but do not react with other components in a cell to form a stable (i.e., irreversible under physiological conditions) covalent bond. Examples of such chemistries are provided below. The result of this step is referenced herein as a "second cross-linked product".

The second cross-linked product can be isolated from other products (e.g., other protein-protein complexes that have not been linked to the oligonucleotide) by, e.g., using the affinity tag or by hybridization of the reaction mix to immobilized nucleic acid that hybridizes to the oligonucleotide used in the oligonucleotide probe, or by using both the affinity tag and the oligonucleotide.

Once the second cross-linked product is isolated, the product can be analyzed. In particular embodiments, the second cross-linked product may be proteolytically digested and the protein component of the product may be analyzed by mass spectrometry (e.g., by tandem mass spectroscopy) or another analytical technique to identify the proteins in the second cross-linked product. Because the nucleotide sequence of the oligonucleotide portion of the oligonucleotide probe is known, the proteins in the second cross-linked product can be identified as being proximal to a defined position in the target RNA (i.e., the position in the RNA to which the oligonucleotide probe is bound). If the nucleotide sequence of the oligonucleotide of the second cross-linked process is not known, then the sequences can be obtained by routine molecular biology methods, e.g., by PCR and subsequent sequencing.

In a particular embodiment, the arms of the protein-protein crosslinker may contain one or more cleavable bonds that may be cleaved prior to analysis of the protein component of the second cross-linked product. Cleavage of these bonds may release the peptides which are crosslinked in the second cross-linked product, facilitating their analysis. While, again, a variety of chemistries may be employed in this cleavage step, in particular embodiments, a chemistry is chosen so that the cleavage occurs under low energy conditions (i.e., conditions that are insufficient to cleave a polypeptide backbone) within a mass spectrometer system (e.g., during ionization, during ion transport, or in a collision cell). In these embodiments, the arms of the crosslinker may contain a sulphonium, phosphonium or ammonium group that is adjacent to (e.g., within 4, 5, 6 or 7 atoms of) a carbonyl group or heterosubstituted carbonyl group, and the reaction may occur via a nucleophilic substitution reaction of the heteroatoms containing at least one lone pair of electrons with atoms that are adjacent to the sulphonium, phosphonium or ammonium leaving groups to break the covalent bonds adjacent to the sulphonium, phosphonium or ammonium leaving groups, releasing positively charged peptide-containing products. The stability of the covalent bonds adjacent to the sulphonium, phosphonium or ammonium leaving groups is such that the bonds are capable of being selectively cleaved in a mass spectrometer system under ionization conditions that do not fragment the backbone of a peptide. Such chemistry is known and described in Amunugama et al., "Mechanisms for the Selective Gas-Phase Fragmentation Reactions of Methionine Side Chain Fixed Charge Sulfonium Ion Containing Peptides," Journal of the American Society for Mass Spectrometry, Volume 17, Issue 12, December 2006, Pages 1631-1642, which is incorporated herein by reference for disclosure of the reaction.

A variety of cleavable and non-cleavable linkers are known to those of skill in the art and find use in the subject crosslinking reagents, e.g., as described in Olejnik et al. (Methods in Enzymology 1998 291:135-154), and further described in U.S. Pat. No. 6,027,890; Olejnik et al. (Proc. Natl. Acad Sci, 92:7590-94); Ogata et al. (Anal. Chem. 2002 74:4702-4708); Bai et al. (Nucl. Acids Res. 2004 32:535-541); Zhao et al. (Anal. Chem. 2002 74:4259-4268); and Sanford et al. (Chem. Mater. 1998 10:1510-20). Cleavable linkers that may be employed in the subject crosslinking reagents include electrophilically cleavable linkers, enzymatically cleavable linkers, nucleophilically cleavable linkers, photocleavable linkers, metal cleavable linkers, electrolytically-cleavable linkers, and linkers that are cleavable under reductive and oxidative conditions. When the biotin moiety is connected to the crosslinking reagent via a cleavable linker, that linker may be selectively cleaved without breaking other cleavable bonds in the molecule (i.e., the cleavable bonds connecting the protein linking groups with the scaffold). Exemplary cleavable linkers useful for connecting to the affinity tag may include photo-sensitive groups comprising bonds that break upon exposure to light of a certain wavelength. Suitable photocleavable linkers for use in the subject crosslinking reagents include ortho-nitrobenzyl-based linkers, phenacyl linkers, alkoxybenzoin linkers, chromium arene complex linkers, NpSSMpact linkers and pivaloylglycol linkers, as described in Guillier et al. (Chem. Rev. 2000 1000:2091-2157). For example, a 1-(2-nitrophenyl)ethyl-based photocleavable linker (Ambergen) can be efficiently cleaved using near-UV light, e.g., in >90% yield in 5-10 minutes using a 365 nm peak lamp at 1-5 mW/cm².

In particular embodiments (and as illustrated in FIG. 1) the method may be performed using a plurality of different oligonucleotide probes that are otherwise identical to one another except for the sequence of the oligonucleotide. The different oligonucleotide probes may be employed in a single reaction (as illustrated in FIG. 1), and the identity of the oligonucleotide present in the second cross-linked product may be identified by PCR and subsequent sequencing. In the embodiment shown, a population of oligonucleotide probes that tile across an RNA of interest may be used.

Reagents

The compounds employed in the method, which are described as being the "first compound" and the "second compound" are described in general and specific terms below. The first compound is of formula I and the second compound is of formula II, as described below:

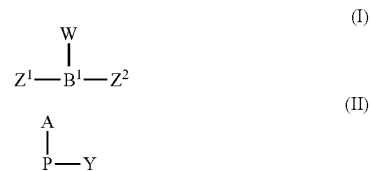

wherein:

$Z^1$ and $Z^2$ are protein reactive groups;

W and Y are conditionally reactive groups that, upon activation, specifically react with one another to covalently link $B^1$ and P;

$B^1$ is a first linking moiety that joins $Z^1$, $Z^2$ and W;

A is an affinity tag; and

P is an oligonucleotide that specifically hybridizes to an RNA of a cell.

A and Y may be positioned anywhere on oligonucleotide P. For example, A may be at or near (i.e., within 20 nucleotides of) the 5' or 3' end or near the middle of P, and, independently A may be at or near (i.e., within 20 nucleotides of) the 5' or 3' end or near the middle of P.

In particular embodiments, W becomes reactive with Y upon addition of a compound that causes W and Y to react. In other embodiments, W may react with Y when they are in close proximity. Such chemistry is described in the following publications, which are incorporated by reference for disclosure of reaction chemistry, reaction conditions, synthesis methods and reactive groups: Shao and Tam, "Unprotected Peptides as Building Blocks for the Synthesis of Peptide Dendrimers with Oxime, Hydrazone, and Thiazolidine Linkages," J. Am. Chem. Soc., 1995, 117 (14), pp 3893-3899; Bertozzi et al., "Copper-free click chemistry for dynamic in vivo imaging", Proc. Natl. Acad. Sci. USA, 2007, 104(43), 16793-7; Franke et al., "Peptide ligation through click chemistry for the generation of assembled and scaffolded peptides," Tetrahedron Letters, 46(26), 2005, 4479-4482; Bertozzi et al., "A 'Traceless' Staudinger Ligation for the Chemoselective Synthesis of Amide Bonds", Org. Lett., 2000, 2 (14), pp 2141-2143; Bertozzi et al., "Incorporation of azides into recombinant proteins for chemoselective modification by the Staudinger ligation," Proc. Natl. Acad. Sci. USA, 2002, 99(1), 19-24. These references are incorporated by reference for disclosure of groups that can participate in such a reaction, and for a description of the chemistry of the reaction.

In particular embodiments, $Z^1$ and $Z^2$ are independently selected from the group consisting of an amino-reactive group, a sulfhydryl reactive group, a hydroxyl reactive group, an imidazolyl reactive group and a guanidinyl reactive group; Y comprises an aldehyde or ketone group; and W comprises a protected hydrazide or amino-oxy group that can be deprotected to produce a hydrazide or amino-oxy group that reacts with Y.

In some embodiments, the protected hydrazide or amino-oxy group can be deprotected using UV light to produce said hydrazide or amino-oxy group. The protected hydrazide or amino-oxy group may contain a photocleavable carbamate protecting group.

In some embodiments, $Z^1$ and $Z^2$ are independently selected from the group consisting of a N-hydroxysuccinimidyl ester, a sulfo-N-hydroxysuccinimidyl ester, a halo-substituted phenol ester, a pentafluorophenol ester, a nitro-substituted phenol ester, an anhydride, an isocyanate, an isothiocyanate, an imidoester, a maleimide and an iodo-acetyl; W is —C(=O)NHNH—$Z^3$, wherein $Z^3$ is the photocleavable carbamate protecting group; A is a biotin affinity tag; and Y comprises an aldehyde group.

In particular embodiments, Y comprises an alkynyl group; W comprises an azido group; and W and Y can react in the presence of an optional catalyst, or when brought into close proximity. In these embodiments, the catalyst may be a copper catalyst.

In some embodiments, Y may comprise a phosphino group and an ester group; and W comprises an azido group; wherein said azido group can be activated by the phosphine group to produce an amino group that reacts with the ester group to covalently link $B^1$ and $B^2$.

In a particular embodiment, Y may be of the structure:

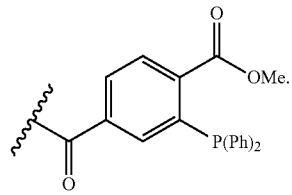

Synthesis

In certain cases, a plurality of sets of oligonucleotide probes may be used, wherein each set of oligonucleotides is directed to a particular RNA and is used in a single reaction. In cases where a plurality of sets of oligonucleotide-probes is employed, the plurality of sets of oligonucleotides may be made using methods adapted from U.S. patent application Ser. No. 12/200,675, filed on Aug. 28, 2008 and published as US20100055681. In these embodiments, the probe oligonucleotides may be amplified from an oligonucleotide composition that contains a mixture of at least 5 of sets of oligonucleotides where each of the sets of oligonucleotides contains at least 10 different oligonucleotides of the following formula $X_1$—V—$X_2$ (from 5' to 3'), where $X_1$ and $X_2$ provide binding sites for a pair of PCR primers (e.g., where $X_1$ has the same sequence as a first PCR primer and $X_2$ has a sequence that is complementary to a second PCR primer), and V is a variable region that has a variable nucleotide sequence that is complementary in an RNA. Within each set, the oligonucleotides may hybridize to different regions of a single RNA, e.g., in a tiled manner. The oligonucleotide composition may be made by synthesizing a plurality of oligonucleotides in situ on a support in the form of an array, and cleaving the oligonucleotide from the support to produce the mixture.

In one embodiment, a set of probe oligonucleotides may be made from an oligonucleotide composition by PCR, where the primer amplifying the sense strand (i.e., the same sequence as the target RNA) has a phosphate on the 5' end, and the primer amplifying the antisense strand has a reactive group and affinity handle cassette, e.g., at the 5' end, as described above. As noted above, the reactive group may be an aldehyde moiety that will react with amino-oxy or hydrazide groups on proteins in the immediate vicinity that have been crosslinked to each other once a photo-induced deprotection is employed. The sense strand of the PCR duplexes can be removed using lambda exonuclease, which specifically removes the 5'-phosphorylated strand of a DNA duplex. After exonuclease treatment, a single-stranded amplified antisense library is left that may tile along the RNA of interest and contains a crosslinking group and an affinity handle at the 5' end. The library may be transferred into living cells by standard techniques such as lipo-fectamine or cell-penetrating peptides, or applied directly to cell lysates. In one embodiment, an oligonucleotide containing a functional group (e.g., 5-thio-U) may be synthesized, and that oligonucleotide may be conjugated to a compound that provides A and Y.

Compound I and compound II can be made by any of a number of methods, the steps of which employ known chemistry and commercially available reagents.

The following is an example of Compound I:

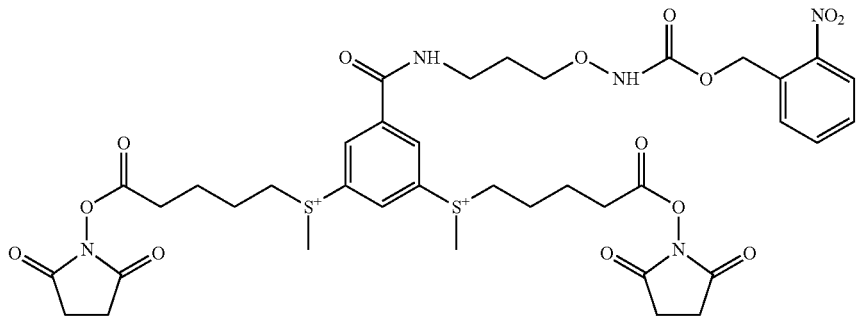 [SMILES: C[S+](CCCCC(=O)ON1C(=O)CCC1=O)c1cc(C(=O)NCCCONC(=O)OCc2ccccc2[N+](=O)[O-])cc([S+](C)CCCCC(=O)ON2C(=O)CCC2=O)c1]

This exemplary compound can be reacted with proteins and ultimately deprotected and reacted with the aldehyde. Synthesis of the compound may be done as follows:

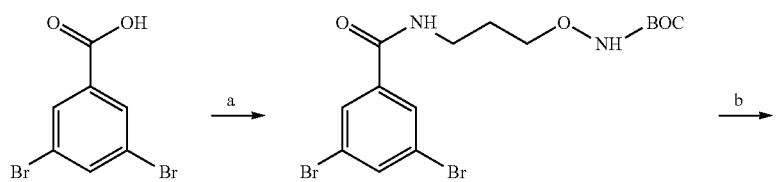

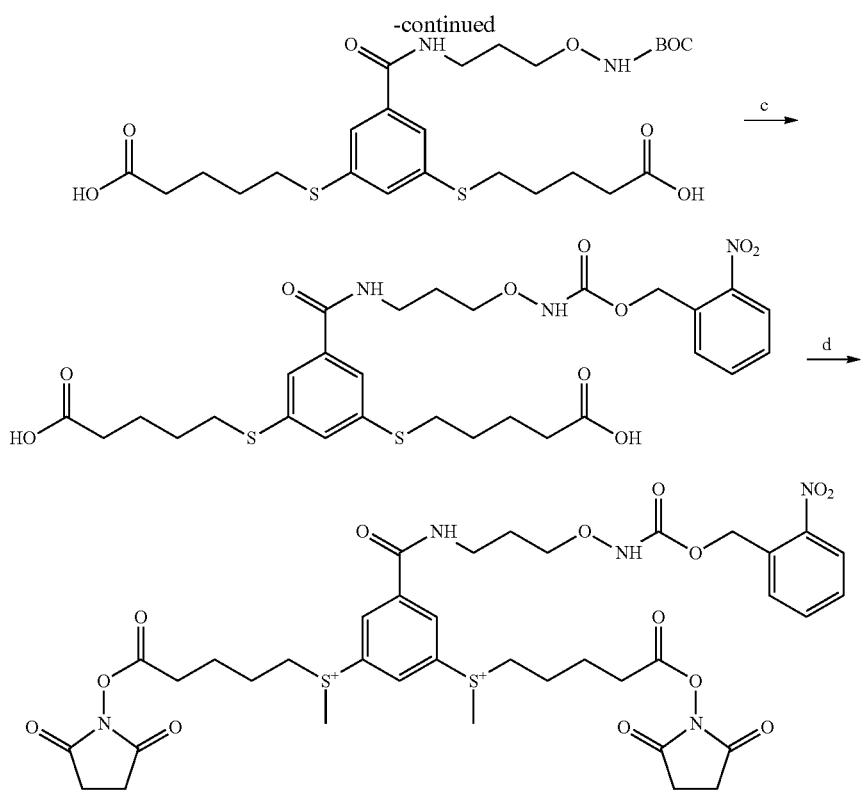
a) DCC, H$_2$N(CH$_2$)$_3$ONHBoc; b) Thiovaleric acid, Pd(OAc)$_2$; c) 1) TFA, 2) 2-nitrobenzyl chloroformate; d) 1) DCC, NHS, 2) MeI, AgBF$_4$.
The following compound can be reacted with an oligonucleotides containing a 5-thio-U to produce an example of Compound II:
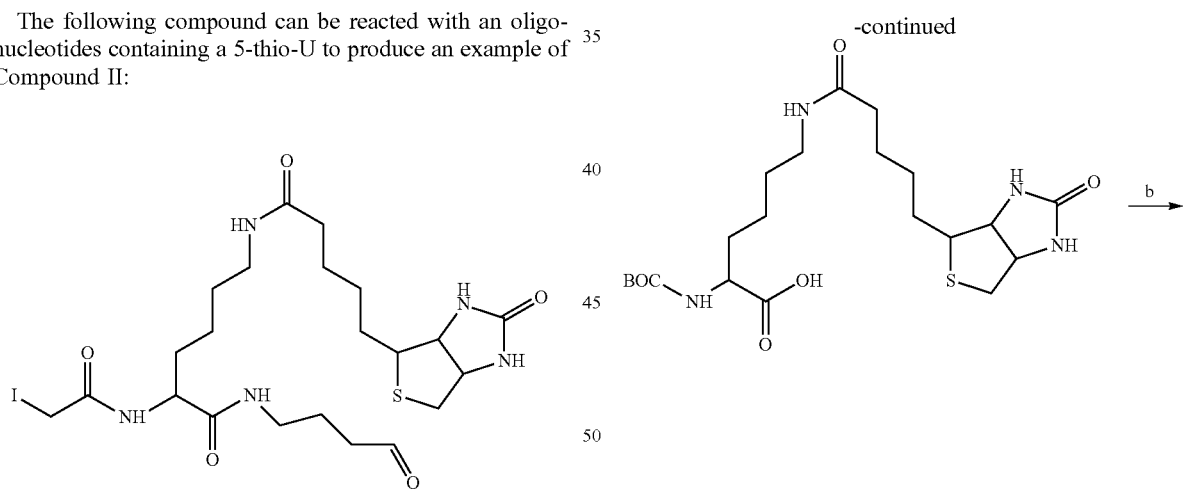
Synthesis of this compound may be done as follows:
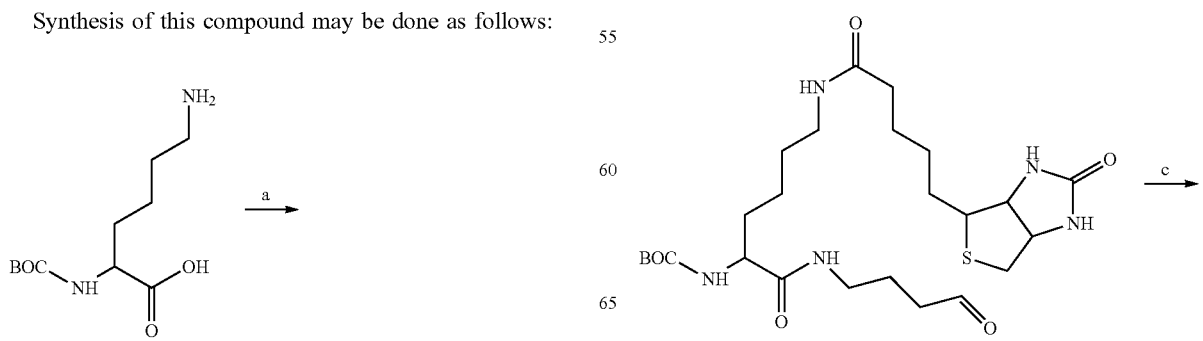

-continued

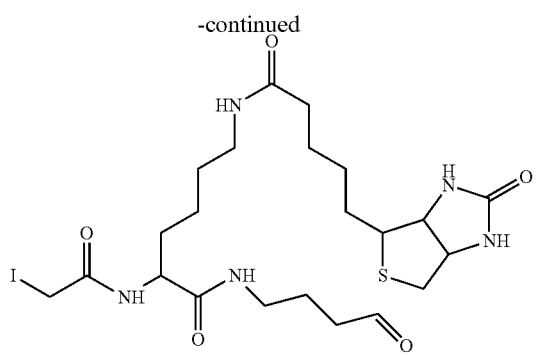

a) Biotin-PfP; b) DCC, H$_2$N(CH$_2$)$_3$CHO; c) 1) TFA; 2) DCC, ICH$_2$COOH.

Methods of Sample Analysis

Also provided is a method of sample analysis. In certain embodiments, this method comprises: a) obtaining a first compound and a second compound, as described above; b) cross-linking protein of a cell using said first compound to produce a first cross-linked product comprising cross-linked protein, and RNA; c) contacting said first cross-linked product and said second compound under conditions by which said oligonucleotide hybridizes to said RNA; d) activating the reaction between W and Y, thereby covalently crosslinking said oligonucleotide to said cross-linked protein to produce a second cross-linked product complex comprising affinity tag A and oligonucleotide P; e) isolating the second cross-linked product; and f) analyzing the isolated second cross-linked product. The cross-linked product may be isolated using affinity tag A, and/or by hybridization of the oligonucleotide portion of the molecule.

In particular embodiments, the method comprises adding an activating agent to the product of step c) that causes W and Y to react. However, in certain cases as discussed above, (e.g., when the reaction occurs via CLICK chemistry) this reaction occurs when the two groups are brought into very close proximity.

The method finds use both in the analysis of cell free samples (e.g., samples that include two or more isolated proteins, or a cell lysate) and samples that include intact cells (e.g., a tissue sample or cells grown in culture).

In certain cases, the analyzing comprises amplifying and obtaining the nucleotide sequence of oligonucleotide P, and the analyzing may also involve analyzing the protein component of said second cross-linked product by mass spectrometry.

In particular embodiments, the method may further comprise digesting the protein component of said second cross-linked product using a protease (e.g., trypsin) to fragment said protein component prior to analysis.

In some embodiments, and again depending on the chemistry used, the protein component of said second cross-linked product is cleaved from the affinity tag A and said oligonucleotide P between steps e) and f) of the method, thereby releasing the peptides for analysis.

The method may be multiplexed in that several different first compounds may be employed, where the oligonucleotide sequences of those compounds differ from one another. In these embodiments, the method may comprise contacting the protein of a cell with a plurality of different first compounds, wherein said different first compounds differ from each other in the nucleotide sequence of P. In particular cases, the different first compounds may be designed to tile across an RNA.

The analyzing step of the method may determine the identity of a protein in said second cross-linked product and also identify the nucleotide sequence of the oligonucleotide to which said protein is crosslinked.

Kits

Also contemplated are kits for practicing the above described subject method. The subject kits contain at least the first and second compounds. The kit may also contain reagents for cross-linking, affinity purification, PCR, etc., and may also contain positive and/or negative controls to be run in conjunction with an assay. The various components of the kit may be present in separate containers or certain compatible components may be pre-combined into a single container, as desired.

In addition to above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or downloaded.

The invention claimed is:

1. A kit comprising a first compound of formula I and a second compound of formula II:

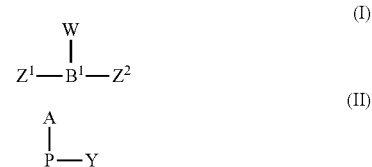

wherein:
  Z$^1$ and Z$^2$ are protein reactive groups;
  W and Y are conditionally reactive groups that, upon activation, specifically react with one another to covalently link B$^1$ and P;
  B$^1$ is a first linking moiety that joins Z$^1$, Z$^2$ and W;
  A is an affinity tag; and
  P is an oligonucleotide that specifically hybridizes to an RNA of a cell.

2. The kit of claim 1, wherein W becomes reactive with Y upon addition of a compound that causes W and Y to react.

3. The kit of claim 1, wherein:
  Z$^1$ and Z$^2$ are independently selected from the group consisting of an amino-reactive group, a sulfhydryl reactive group, a hydroxyl reactive group, an imidazolyl reactive group and a guanidinyl reactive group;
  Y comprises an aldehyde or ketone group; and
  W comprises a protected hydrazide or amino-oxy group that can be deprotected to produce a hydrazide or amino-oxy group that reacts with Y.

4. The kit of claim 3, wherein said protected hydrazide or amino-oxy group can be deprotected using UV light to produce said hydrazide or amino-oxy group.

5. The kit of claim 4, wherein said protected hydrazide or amino-oxy group comprises a photocleavable carbamate protecting group.

6. The kit of claim 5, wherein:
$Z^1$ and $Z^2$ are independently selected from the group consisting of a N-hydroxysuccinimidyl ester, a sulfo-N-hydroxysuccinimidyl ester, a halo-substituted phenol ester, a pentafluorophenol ester, a nitro-substituted phenol ester, an anhydride, an isocyanate, an isothiocyanate, an imidoester, a maleimide and an iodoacetyl;
W is —C(=O)NHNH—$Z^3$, wherein $Z^3$ is the photocleavable carbamate protecting group;
A is a biotin affinity tag; and
Y comprises an aldehyde group.

7. The kit of claim 1, wherein:
Y comprises an alkynyl group;
W comprises an azido group;
wherein W and Y can react in the presence of a catalyst.

8. The kit of claim 7, wherein the catalyst is a copper catalyst.

9. The kit of claim 1, wherein:
Y comprises a phosphino group and an active ester group; and
W comprises an azido group;
wherein said azido group can be activated by said phosphine group to produce an amino group that reacts with said active ester group to covalently link $B^1$ and $B^2$.

10. The kit of claim 9, wherein Y is:

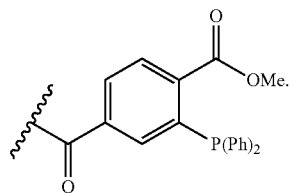

* * * * *